United States Patent
Forsell

(10) Patent No.: US 8,096,938 B2
(45) Date of Patent: *Jan. 17, 2012

(54) CONTROLLED ANAL INCONTINENCE DISEASE TREATMENT

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 545 days.

This patent is subject to a terminal disclaimer.

(21) Appl. No.: 10/270,719

(22) Filed: Oct. 16, 2002

(65) Prior Publication Data

US 2003/0088148 A1    May 8, 2003

Related U.S. Application Data

(63) Continuation of application No. 09/502,089, filed on Feb. 10, 2000, now Pat. No. 6,503,189.

(60) Provisional application No. 60/148,345, filed on Aug. 12, 1999.

(51) Int. Cl.
    *A61F 2/02*    (2006.01)
(52) U.S. Cl. .......................................... 600/30
(58) Field of Classification Search ............. 600/29–32, 600/37; 128/897–898, DIG. 25
    See application file for complete search history.

(56) References Cited

U.S. PATENT DOCUMENTS

| | | |
|---|---|---|
| 2,060,913 A | 11/1936 | Weaver |
| 2,795,641 A | 6/1957 | Ross |
| 3,209,081 A | 9/1965 | Behrman et al. |
| 3,598,287 A | 8/1971 | De Man |
| 3,692,027 A | 9/1972 | Ellinwood, Jr. |
| 3,731,679 A | 5/1973 | Wilhelmson et al. |
| 3,731,681 A | 5/1973 | Blackshear et al. |
| 3,750,194 A | 8/1973 | Summers |
| 3,817,237 A | 6/1974 | Bolduc |
| 3,855,122 A | 12/1974 | Bourganel |
| 3,875,928 A | 4/1975 | Angelchik |
| 3,923,060 A | 12/1975 | Ellinwood, Jr. |
| 3,954,102 A | 5/1976 | Buuck |
| 4,003,379 A | 1/1977 | Ellinwood, Jr. |
| 4,009,711 A | 3/1977 | Uson |
| 4,026,305 A | 5/1977 | Brownlee et al. |
| 4,044,401 A | 8/1977 | Guiset |

(Continued)

FOREIGN PATENT DOCUMENTS

DE    19511998    10/1996

(Continued)

OTHER PUBLICATIONS

International Search Report from corresponding International Application No. PCT/SE01/00254, mailed Jun. 25, 2001.
Publication No. EP 1568338A2, dated Aug. 31, 2005, for European Patent Application No. 05010107.0.
European Search Report, dated Sep. 14, 2006, for EP 05010107.0.
Examination Report, dated Nov. 4, 2008, in European Patent Application No. 05010107.0.
U.S. Appl. No. 11/988,450, Forsell.

(Continued)

*Primary Examiner* — Samuel G Gilbert
(74) *Attorney, Agent, or Firm* — Nixon & Vanderhye P.C.

(57) ABSTRACT

An anal incontinence disease treatment apparatus and method include and use an operable restriction device implanted in a patient and engaging the colon or engaging the rectum to form a restricted fecal passageway in the colon or rectum. A source of energy for energizing the restriction device is provided, as well as a control device for releasing energy from the source of energy from outside the patient's body. The released energy is used in connection with the operation of the restriction device, i.e. to enlarge and contract the fecal passageway to allow or substantially prevent passage of fecal material through the passageway.

62 Claims, 6 Drawing Sheets

U.S. PATENT DOCUMENTS

| | | | |
|---|---|---|---|
| 4,201,202 A | 5/1980 | Finney et al. | |
| 4,221,219 A | 9/1980 | Tucker | |
| 4,235,222 A | 11/1980 | Ionescu | |
| 4,243,306 A | 1/1981 | Bononi | |
| 4,246,893 A | 1/1981 | Berson | |
| 4,265,241 A | 5/1981 | Portner et al. | |
| 4,271,827 A | 6/1981 | Angelchik | |
| 4,274,407 A | 6/1981 | Scarlett | |
| 4,303,225 A | 12/1981 | Freeman | |
| 4,304,225 A | 12/1981 | Freeman | |
| 4,318,396 A | 3/1982 | Finney | |
| 4,342,308 A | 8/1982 | Trick | |
| 4,369,771 A | 1/1983 | Trick | |
| 4,400,169 A | 8/1983 | Stephens | |
| 4,412,530 A | 11/1983 | Burton | |
| 4,424,807 A | 1/1984 | Evans | |
| 4,505,710 A | 3/1985 | Collins | |
| 4,509,947 A | 4/1985 | Lattin | |
| 4,542,753 A | 9/1985 | Brenman et al. | |
| 4,550,720 A | 11/1985 | Trick | |
| 4,556,050 A | 12/1985 | Hodgson et al. | |
| 4,559,930 A | 12/1985 | Cobiski | |
| 4,559,939 A | 12/1985 | Cobiski | |
| 4,563,175 A | 1/1986 | LaFond | |
| 4,583,523 A | 4/1986 | Kleinke et al. | |
| 4,584,994 A | 4/1986 | Bamberger et al. | |
| 4,592,339 A | 6/1986 | Kuzmak et al. | |
| 4,592,355 A | 6/1986 | Antebi | |
| 4,599,081 A | 7/1986 | Cohen | |
| 4,602,621 A | 7/1986 | Hakky | |
| 4,610,658 A | 9/1986 | Buchwald et al. | |
| 4,623,350 A | 11/1986 | Lapeyre et al. | |
| 4,628,928 A | 12/1986 | Lowell | |
| 4,664,100 A | 5/1987 | Rudloff | |
| 4,677,534 A | 6/1987 | Okochi | |
| 4,679,560 A | 7/1987 | Galbraith | |
| 4,696,288 A | 9/1987 | Kuzmak et al. | |
| 4,711,231 A | 12/1987 | Finegold et al. | |
| 4,723,538 A | 2/1988 | Stewart et al. | |
| 4,756,949 A | 7/1988 | Spence et al. | |
| 4,771,780 A | 9/1988 | Sholder | |
| 4,828,544 A | 5/1989 | Lane et al. | |
| 4,828,990 A | 5/1989 | Higashi et al. | |
| 4,829,990 A | 5/1989 | Thuroff et al. | |
| 4,846,794 A | 7/1989 | Hertzer | |
| 4,902,279 A | 2/1990 | Schmidtz et al. | |
| 4,925,443 A | 5/1990 | Heilman et al. | |
| 4,941,461 A | 7/1990 | Fischell | |
| 4,942,668 A | 7/1990 | Franklin | |
| 4,958,630 A | 9/1990 | Rosenbluth et al. | |
| 4,979,955 A | 12/1990 | Smith | |
| 4,982,731 A | 1/1991 | Lue et al. | |
| 5,006,106 A | 4/1991 | Angelchik | |
| 5,012,822 A | 5/1991 | Schwarz | |
| 5,042,084 A | 8/1991 | Daly | |
| 5,048,511 A | 9/1991 | Rosenbluth et al. | |
| 5,057,075 A | 10/1991 | Moncrief et al. | |
| 5,062,416 A | 11/1991 | Stucks | |
| 5,066,278 A | 11/1991 | Hirschberg et al. | |
| 5,074,868 A | 12/1991 | Kuzmak | |
| 5,098,369 A | 3/1992 | Heilman et al. | |
| 5,112,202 A | 5/1992 | Oshima et al. | |
| 5,123,428 A | 6/1992 | Schwarz | |
| 5,160,338 A | 11/1992 | Vincent | |
| 5,226,429 A | 7/1993 | Kuzmak | |
| 5,250,020 A | 10/1993 | Bley | |
| 5,297,536 A | 3/1994 | Wilk | |
| 5,304,206 A | 4/1994 | Baker, Jr. et al. | |
| 5,316,543 A | 5/1994 | Eberbach | |
| 5,358,474 A | 10/1994 | Kaldany | |
| 5,415,660 A | 5/1995 | Campbell et al. | |
| 5,437,605 A | 8/1995 | Helmy | |
| 5,449,368 A | 9/1995 | Kuzmak | |
| 5,453,079 A | 9/1995 | Schwaninger | |
| 5,454,840 A | 10/1995 | Krakovsky et al. | |
| 5,501,703 A | 3/1996 | Holsheimer et al. | |
| 5,505,733 A | 4/1996 | Justin et al. | |
| 5,509,888 A * | 4/1996 | Miller | 600/29 |
| 5,518,504 A | 5/1996 | Polyak | |
| 5,540,731 A | 7/1996 | Testerman | |
| 5,569,187 A | 10/1996 | Kaiser | |
| 5,578,069 A | 11/1996 | Miner, II | |
| 5,582,580 A | 12/1996 | Buckman, Jr. et al. | |
| 5,665,065 A | 9/1997 | Colman et al. | |
| 5,676,674 A | 10/1997 | Bolanos et al. | |
| 5,690,108 A | 11/1997 | Chakeres | |
| 5,702,431 A | 12/1997 | Wang et al. | |
| 5,704,893 A * | 1/1998 | Timm | 600/29 |
| 5,735,887 A | 4/1998 | Barreras et al. | |
| 5,749,909 A | 5/1998 | Schroeppel et al. | |
| 5,769,877 A | 6/1998 | Barreras | |
| 5,771,903 A | 6/1998 | Jakobsson | |
| 5,814,020 A | 9/1998 | Gross | |
| 5,823,991 A | 10/1998 | Shim | |
| 5,827,286 A | 10/1998 | Incavo et al. | |
| 5,848,962 A | 12/1998 | Feindt et al. | |
| 5,858,001 A | 1/1999 | Tsals et al. | |
| 5,876,425 A | 3/1999 | Gord et al. | |
| 5,900,909 A | 5/1999 | Parulski et al. | |
| 5,902,336 A | 5/1999 | Mishkin | |
| 5,910,149 A | 6/1999 | Kuzmak | |
| 5,928,195 A | 7/1999 | Malamud et al. | |
| 5,938,584 A | 8/1999 | Ardito et al. | |
| 5,938,669 A | 8/1999 | Klaiber et al. | |
| 5,978,712 A | 11/1999 | Suda et al. | |
| 5,995,874 A | 11/1999 | Borza | |
| 5,997,501 A | 12/1999 | Gross et al. | |
| 6,003,736 A | 12/1999 | Ljunggren | |
| 6,067,991 A | 5/2000 | Forsell | |
| 6,074,341 A | 6/2000 | Anderson et al. | |
| 6,077,215 A | 6/2000 | Leysieffer | |
| 6,095,968 A | 8/2000 | Snyders | |
| 6,102,887 A | 8/2000 | Altman | |
| 6,102,922 A | 8/2000 | Jakobsson et al. | |
| 6,113,574 A | 9/2000 | Spinello | |
| 6,117,067 A | 9/2000 | Gil-Vernet | |
| 6,134,470 A | 10/2000 | Hartlaub | |
| 6,135,945 A | 10/2000 | Sultan | |
| 6,162,238 A | 12/2000 | Kaplan et al. | |
| 6,185,452 B1 | 2/2001 | Schulman et al. | |
| 6,197,055 B1 | 3/2001 | Matthews | |
| 6,210,347 B1 | 4/2001 | Forsell | |
| 6,221,060 B1 | 4/2001 | Willard | |
| 6,233,474 B1 | 5/2001 | Lemelson | |
| 6,275,737 B1 | 8/2001 | Mann | |
| 6,319,191 B1 | 11/2001 | Sayet et al. | |
| 6,346,099 B1 | 2/2002 | Altman | |
| 6,436,054 B1 | 8/2002 | Viola et al. | |
| 6,450,173 B1 | 9/2002 | Forsell | |
| 6,450,946 B1 | 9/2002 | Forsell | |
| 6,453,907 B1 | 9/2002 | Forsell | |
| 6,454,698 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,456,883 B1 | 9/2002 | Torgerson et al. | |
| 6,460,543 B1 | 10/2002 | Forsell | |
| 6,461,292 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,470,892 B1 | 10/2002 | Forsell | |
| 6,471,635 B1 | 10/2002 | Forsell | |
| 6,475,136 B1 | 11/2002 | Forsell | |
| 6,482,145 B1 | 11/2002 | Forsell | |
| 6,911,002 B2 | 12/2002 | Fierro | |
| 6,503,189 B1 | 1/2003 | Forsell | |
| 6,572,585 B2 | 6/2003 | Choi | |
| 6,589,229 B1 | 7/2003 | Connelly et al. | |
| 6,638,208 B1 | 10/2003 | Natarajan et al. | |
| 6,638,303 B1 | 10/2003 | Campbell | |
| 6,659,936 B1 | 12/2003 | Furness et al. | |
| 6,678,561 B2 | 1/2004 | Forsell | |
| 6,689,085 B1 | 2/2004 | Rubenstein et al. | |
| 6,709,385 B2 | 3/2004 | Forsell | |
| 6,740,075 B2 | 5/2004 | Lebel et al. | |
| 6,772,011 B2 | 8/2004 | Dolgin | |

| Patent/Pub No. | Date | Name |
|---|---|---|
| 6,895,280 B2 | 5/2005 | Meadows et al. |
| 6,915,165 B2 | 7/2005 | Forsell |
| 6,929,625 B2 | 8/2005 | Bierman |
| 6,948,918 B2 | 9/2005 | Hansen |
| 6,953,429 B2 | 10/2005 | Forsell |
| 6,960,233 B1 | 11/2005 | Berg et al. |
| 6,979,351 B2 | 12/2005 | Forsell et al. |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,207,936 B2 | 4/2007 | Forsell |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 2001/0011543 A1 | 8/2001 | Forsell |
| 2002/0022759 A1 | 2/2002 | Forsell |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0095139 A1 | 7/2002 | Keogh et al. |
| 2002/0095164 A1 | 7/2002 | Andreas |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Forsell |
| 2003/0144648 A1 | 7/2003 | Forsell |
| 2003/0163029 A1 | 8/2003 | Sonnenschein et al. |
| 2003/0208247 A1 | 11/2003 | Spinelli et al. |
| 2003/0233143 A1 | 12/2003 | Gharib et al. |
| 2004/0024285 A1 | 2/2004 | Muckter |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0249451 A1 | 12/2004 | Lu et al. |
| 2004/0260316 A1 | 12/2004 | Knudson et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0222678 A1 | 10/2005 | Lashinski et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2006/0025855 A1 | 2/2006 | Lashinski et al. |
| 2006/0069414 A1 | 3/2006 | Imran et al. |
| 2006/0127246 A1 | 6/2006 | Forsell |
| 2006/0142635 A1 | 6/2006 | Forsell |
| 2006/0149124 A1 | 7/2006 | Forsell |
| 2006/0167539 A1 | 7/2006 | Mcewan |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0049790 A1 | 3/2007 | Wagner et al. |
| 2007/0073099 A1 | 3/2007 | Forsell |
| 2007/0092862 A1 | 4/2007 | Gerber |
| 2007/0156204 A1 | 7/2007 | Denker et al. |
| 2007/0167670 A1 | 7/2007 | Coleman et al. |
| 2007/0193632 A1 | 8/2007 | Shu |
| 2007/0204924 A1 | 9/2007 | Delgiacco et al. |
| 2007/0225802 A1 | 9/2007 | Forsell |
| 2007/0232848 A1 | 10/2007 | Forsell |
| 2007/0233019 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfield |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0200753 A1 | 8/2008 | Forsell |
| 2008/0214888 A1 | 9/2008 | Shalom |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0054725 A1 | 2/2009 | Forsell |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2010/0145138 A1 | 6/2010 | Forsell |
| 2010/0145139 A1 | 6/2010 | Forsell |
| 2010/0217067 A1 | 8/2010 | Forsell |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Finitsis |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |

FOREIGN PATENT DOCUMENTS

| | | |
|---|---|---|
| EP | 0102548 | 3/1984 |
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 | 11/1994 |
| EP | 0626154 A1 | 11/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 514 526 | 3/2005 |
| EP | 1563814 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 913 880 | 4/2008 |
| FR | 2688693 | 9/1993 |
| FR | 2692777 | 12/1993 |
| FR | 27565485 | 6/1998 |
| FR | 2797181 | 2/2001 |
| GB | 8 856 74 | 12/1961 |
| GB | 1194358 | 6/1970 |
| WO | 84/01282 | 4/1984 |
| WO | 94/27504 | 12/1994 |
| WO | 96/01597 | 1/1996 |
| WO | 96/11036 | 4/1996 |
| WO | WO 96/39932 | 12/1996 |
| WO | 97/41799 | 11/1997 |
| WO | WO 98/06358 | 2/1998 |
| WO | WO 98/50099 | 11/1998 |
| WO | 99/18885 | 4/1999 |
| WO | 00/09047 | 2/2000 |
| WO | 00/09048 | 2/2000 |
| WO | WO 00/09048 | 2/2000 |
| WO | 00/15158 | 3/2000 |
| WO | WO 00/16686 | 3/2000 |
| WO | 0112078 | 2/2001 |
| WO | WO 01/12108 | 2/2001 |
| WO | WO 01/45487 | 6/2001 |
| WO | WO 01/45590 | 6/2001 |
| WO | 01/47431 | 7/2001 |
| WO | 0147434 | 7/2001 |
| WO | WO 01/47575 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | 02/40083 | 5/2002 |
| WO | WO 02/38217 | 5/2002 |
| WO | WO 02/053210 | 7/2002 |
| WO | WO 02/058563 | 8/2002 |
| WO | 02/087657 | 11/2002 |
| WO | WO 02/100481 | 12/2002 |
| WO | WO 03/002192 | 1/2003 |
| WO | WO 03/033054 | 4/2003 |
| WO | 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 2005/072169 | 8/2005 |
| WO | WO 2005/105003 | 11/2005 |
| WO | WO 2006/122285 | 11/2006 |
| WO | WO 2006/134106 | 12/2006 |
| WO | WO 2007/017880 | 2/2007 |
| WO | 0147435 | 4/2007 |
| WO | WO 2007/041795 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

European Examination Report for EP 05 010 0460.0, dated May 19, 2006 (4 Pages).
Websters II New River side University, 1984, pp. 573,1000.
U.S. Appl. No. 12/839,115.
U.S. Appl. No. 12/839,162.
U.S. Appl. No. 12/859,454.
U.S. Appl. No. 12/864,695.
U.S. Appl. No. 12/864,702.
U.S. Appl. No. 12/864,706.
U.S. Appl. No. 12/864,708.
U.S. Appl. No. 12/864,714.
U.S. Appl. No. 12/864,718.
U.S. Appl. No. 12/864,724.
U.S. Appl. No. 12/864,828.
U.S. Appl. No. 12/864,833.
U.S. Appl. No. 12/864,836.
U.S. Appl. No. 12/864,843.
U.S. Appl. No. 12/864,845.
U.S. Appl. No. 12/864,849.
U.S. Appl. No. 12/864,852.
U.S. Appl. No. 12/864,855.
U.S. Appl. No. 12/864,943.
U.S. Appl. No. 12/864,947.
U.S. Appl. No. 12/864,952.
U.S. Appl. No. 12/864,982.
U.S. Appl. No. 12/865,015.
U.S. Appl. No. 12/865,033.
U.S. Appl. No. 12/865,044.
U.S. Appl. No. 12/865,061.
U.S. Appl. No. 12/865,071.
U.S. Appl. No. 09/373,224, Forsell.
U.S. Appl. No. 13/080,118, Forsell.
U.S. Appl. No. 13/122,809, Forsell.
U.S. Appl. No. 13/122,825, Forsell.
U.S. Appl. No. 13/122,907, Forsell.
U.S. Appl. No. 13/123,019, Forsell.
U.S. Appl. No. 13/123,025, Forsell.
U.S. Appl. No. 13/123,037, Forsell.
U.S. Appl. No. 13/123,041, Forsell.
U.S. Appl. No. 13/123,082, Forsell.
U.S. Appl. No. 13/123,151, Forsell.
U.S. Appl. No. 13/123,182, Forsell.
U.S. Appl. No. 13/123,197, Forsell.
U.S. Appl. No. 13/123,145, Forsell.
U.S. Appl. No. 13/123,183, Forsell.
U.S. Appl. No. 13/123,231, Forsell.
U.S. Appl. No. 13/123,232, Forsell.
U.S. Appl. No. 13/123,255, Forsell.
U.S. Appl. No. 13/123,261, Forsell.
U.S. Appl. No. 13/123,284, Forsell.
U.S. Appl. No. 13/123,330, Forsell.
U.S. Appl. No. 13/123,394, Forsell.
U.S. Appl. No. 13/123,402, Forsell.
U.S. Appl. No. 13/123,425, Forsell.
U.S. Appl. No. 13/123,436, Forsell.
U.S. Appl. No. 13/123,446, Forsell.
U.S. Appl. No. 13/123,536, Forsell.
U.S. Appl. No. 13/123,537, Forsell.
U.S. Appl. No. 13/123,583, Forsell.
U.S. Appl. No. 13/123,586, Forsell.
U.S. Appl. No. 13/123,587, Forsell.
U.S. Appl. No. 13/123,667, Forsell.

* cited by examiner

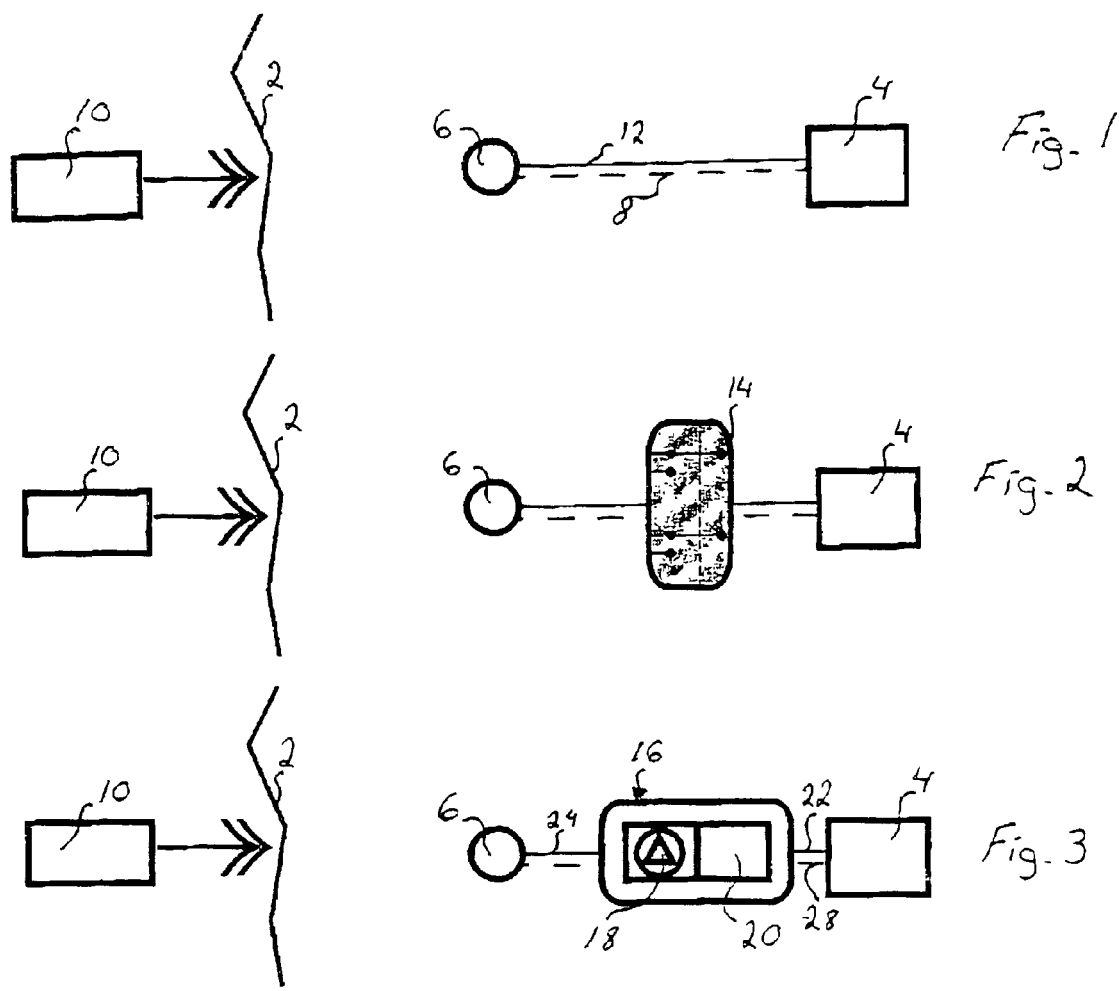

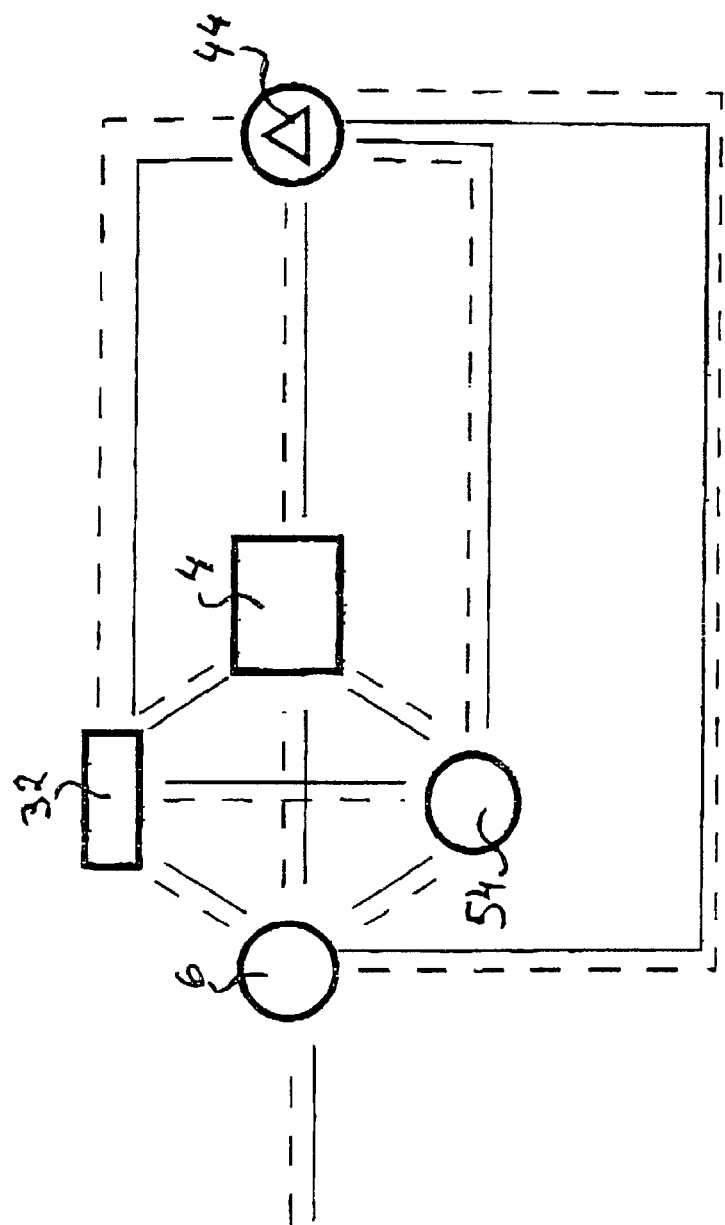
Fig. 9
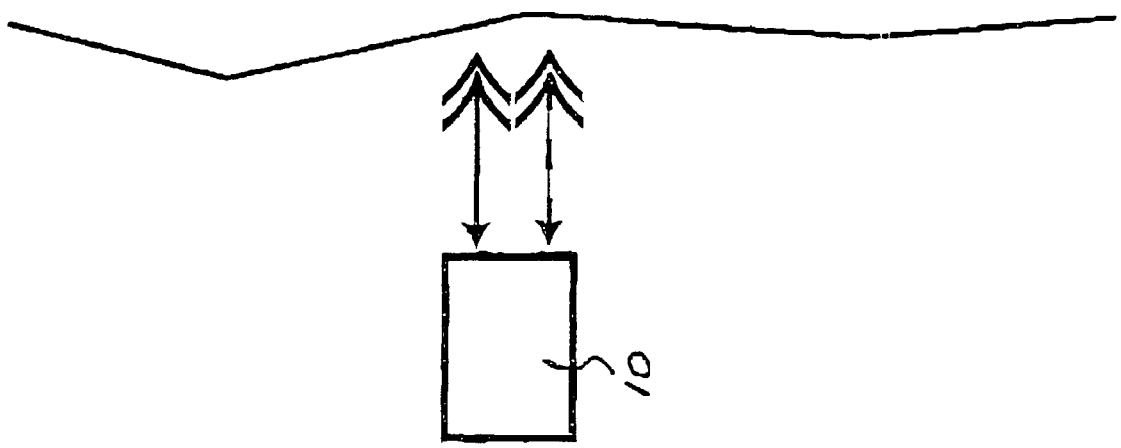

CONTROLLED ANAL INCONTINENCE DISEASE TREATMENT

CROSS REFERENCE TO RELATED APPLICATION

This application is a continuation of application Ser. No. 09/502,089, filed Feb. 10, 2000, now U.S. Pat. No. 6,503,189, issued Jan. 7, 2003, which incorporates herein by reference the disclosure of Provisional Application Ser. No. 60/148,345, filed Aug. 12, 1999.

BACKGROUND OF THE INVENTION

The present invention relates to an anal incontinence disease treatment apparatus and method. More specifically, the invention relates to an anal incontinence disease treatment apparatus and method for surgical application in the abdomen of a patient for forming a restricted fecal passageway in the colon or rectum. The term patient includes an animal or a human being.

Anal incontinence disease is a widespread medical problem. Several kinds of sphincter plastic surgery are used today to remedy anal incontinence. There is a prior manually operated sphincter system in an initial clinical trial phase where a hydraulic sphincter system connected to a reservoir placed in the scrotum is developed. A disadvantage of this system is that thick, hard fibrosis is created around the reservoir by pump movements making the system useless sooner or later.

U.S. Pat. No. 5,593,443 discloses a hydralic anal sphincter under both reflex and voluntary control. A pressure controlled inflatable artificial sphincter is desclosed in U.S. Pat. No. 4,222,377.

SUMMARY OF THE INVENTION

It is an object of the present invention to provide a new convenient anal incontinence disease treatment apparatus, the performance of which may be affected by the patient at any time after operation, in particular when various needs arise over the day, so that the patient always is satisfied.

Accordingly, there is provided an anal incontinence disease treatment apparatus, comprising an operable restriction device implanted in a patient and engaging the or engaging the rectum to form a restricted fecal passageway in the colon or rectum, a source of energy for energizing the restriction device, and a control device operable from outside the patient's body for releasing energy from the source of energy, wherein the released energy is used in connection with the operation of the restriction device.

As a result, the advantage is achieved that the implanted restriction device can be non-invasively operated, when the restriction device has to be adjusted. Furthermore, the apparatus of the invention provides a simple and effective control of the energy supplied to implanted components of the apparatus which ensures long reliable function of the apparatus, possibly for the rest of the patient's life.

The restriction device preferably controls the cross-sectional area of the fecal passageway in the colon or rectum, which gives the advantage that the patient is enabled to adjust the cross-sectional area of the fecal passageway whenever he likes during the day. This advantage should not be underestimated, because in case the patient would need to vomit it would be very difficult for him to do so if he were unable to immediately enlarge the cross-sectional area of the fecal passageway.

The control device may also control the restriction device. The control device may comprise an internal control unit, preferably including a microprocessor, implanted in the patient for controlling the restriction device. The control device may further comprise an external control unit outside the patient's body, wherein the internal control unit is programmable by the external control unit, for example for controlling the restriction device over time. Alternatively, the internal control unit may control the restriction device over time in accordance with an activity schedule program, which may be adapted to the patient's needs.

Conveniently, the external control unit may load the internal control unit with data in accordance with a loading mode only authorized for a doctor. For specialized controls of the restriction device, the external control unit may control the internal control unit in accordance with a doctor mode only authorized for the doctor. For simple controls of the restriction device, the external control unit may control the internal control unit in accordance with a patient mode permitted for the patient. Thus, by using the external control unit in accordance with different modes it is possible to have certain functions of the restriction device controlled by the patient and other more advanced functions controlled by the doctor resulting, which enables a flexible post-operation treatment of the patient.

Generally, the apparatus further comprises an operation device implanted in the patient for operating the restriction device, wherein the control device controls the operation device to operate the restriction device. The control device may directly power the operation device with energy released from the source of energy and/or power other implanted energy consuming components of the apparatus. The term "directly" is used to mean, on one hand, that the operation device is powered with released energy while the latter is being released by the control device, on the other hand, that the released energy may be somewhat delayed, in the order of seconds, by for instance an energy stabilizer before powering the operation device. The advantage of directly using energy as it is released is that the apparatus can be of a very simple design and the few components involved makes the apparatus extremely reliable.

The restriction device may be non-inflatable, i.e. with no hydraulic fluid involved for the adjustments of the restriction device. This eliminates problems with fluid leaking from the restriction device.

The operation device may comprise hydraulic means and at least one valve for controlling a fluid flow in the hydraulic means. The control device may suitably comprise a wireless remote control for controlling the valve. The restriction device may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the source of energy is external to the patient's body and the control device releases wireless energy from the source of energy. An energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy. Where the control device comprises an implanted control unit the electronic circuit thereof and the restriction device may be directly powered with transformed wireless energy, or energy from either the implanted energy storage device or battery.

In a first particular embodiment in accordance with the first main aspect of the invention, the operation device comprises a motor, preferably an electric motor which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first main aspect of the invention, the control device is adapted to shift polarity of the released energy to reverse the operation device. The operation device may suitably comprise an electric motor and the released energy may comprise electric energy.

In a third particular embodiment in accordance with the first main aspect of the invention, the restriction device is operable to perform a reversible function and there is a reversing device implanted in the patient for reversing the function performed by the restriction device. Such a reversing function preferably involves enlarging and restricting the fecal passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a-g ear box.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first main aspect of the invention, the restriction device comprises hydraulic means, for example including an expansible/contractible cavity for fluid. The operation device preferably comprises a pump for pumping a fluid in the hydraulic means, a motor for driving the pump, a valveless fluid conduit between the pump and the hydraulic means of the restriction device, and a reservoir for fluid, wherein the reservoir forms part of the conduit. All of the hydraulic components involved are preferably devoid of any non-return valve. This is of great advantage, because with valves involved there is always a risk of malfunction due to improperly working valves, especially when long time periods passes between valve operations. The reservoir may form a fluid chamber with a variable volume, and the pump may distribute fluid from the chamber to the hydraulic means of the restriction device by reduction of the volume of the chamber and withdraw fluid from the hydraulic means to the chamber by expansion of the volume of the chamber.

In accordance with a second main aspect of the invention, the source of energy is implanted in the patient. Thus, the control device releases energy from the implanted source of energy from outside the patient's body. This solution is advantageous for embodiments of the apparatus that have a relatively high energy consumption which cannot be satisfied by direct supply of wireless energy.

The source of energy thus implanted may comprise an accumulator, preferably an electric source of energy, such as a battery having a life-time of at least 10 years.

The above first, second, third and fourth particular embodiments described in connection with the first main aspect of the invention are also applicable in accordance with the second main aspect of the invention, i.e. where the source of energy is implanted.

All of the above embodiments may be combined with at least one implanted sensor for sensing at least one physical parameter of the patient, wherein the control device may control the restriction device in response to signals from the sensor. For example, the sensor may comprise a pressure sensor for directly or indirectly sensing the pressure in the fecal passageway. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The expression "indirectly sensing the pressure in the fecal passageway" should be understood to encompass the cases where the sensor senses the pressure against the restriction device or human tissue of the patient. Where the control device comprises an internal control unit implanted in the patient, the internal control unit may suitably directly control the restriction device in response to signals from the sensor. In response to signals from the sensor, for example pressure, the patient's position or any other important physical parameter, the internal control unit may send information thereon to outside the patient's body. The control unit may also automatically control the restriction device in response to signals from the sensor. For example, the control unit may control the restriction device to further restrict the fecal passageway in the colon in response to the sensor sensing that the patient is lying, or enlarge the fecal passageway in response to the sensor sensing an abnormally high pressure against the restriction device.

Where the control device comprises an external control unit outside the patient's body, the external control unit may, suitably directly, control the restriction device in response to signals from the sensor. The external control unit may store information on the physical parameter sensed by the sensor and may be manually operated to control the restriction device based on the stored information. In addition, there may be at least one implanted sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted restriction device, back to the external communicator. Alternatively or in combination, the external communicator may feed data to the internal communicator. The implanted communicator may suitably feed data related to at least one physical signal of the patient.

Generally, the apparatus of the invention may comprise a switch implanted in the patient for directly or indirectly switching the energy released from the source of energy. The restriction device may control the cross-sectional area of the fecal passageway. For example, the restriction device may be operable to open and close the fecal passageway or may steplessly control the cross-sectional area of the fecal passageway. A pressure sensor may be provided for directly or indirectly sensing the pressure in the fecal passageway. The control device may control the restriction device in response to signals from the pressure sensor.

The apparatus may comprise an implanted energy transfer device, wherein the control device releases electric energy and the energy transfer device transfers the electric energy into kinetic energy for, preferably direct, operation of the restriction device. Suitably, an implanted stabilizer, such as a capacitor or a rechargeable accumulator, or the like, may be provided for stabilizing the electric energy released by said control device. In addition, the control device may release energy for a determined time period or in a determined number of energy pulses. Finally, the restriction device may be non-inflatable.

All of the above embodiments are preferably remote controlled. Thus, the control device advantageously comprises a wireless remote control transmitting at least one wireless control signal for controlling the restriction device. With such a remote control it will be possible to adapt the function of the apparatus to the patient's need in a daily basis, which is beneficial with respect to the treatment of the patient.

The wireless remote control may be capable of obtaining information on the condition of the implanted restriction device and of controlling the restriction device in response to the information. Also, The remote control may be capable of sending information related to the restriction device from inside the patient'sbody to the outside thereof.

In a particular embodiment of the invention, the wireless remote control comprises at least one external signal transmitter or tranceiver and at least one internal signal receiver or transciever implanted in the patient. In another particular embodiment of the invention, the wireless remote control comprises at least one external signal reciever or transceiver and at least one internal signal transmitter or transceiver implanted in the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

In all of the above solutions, the control device advantageously releases energy from the source of energy in a non-invasive, mechanical or non-mechanical manner.

The control device may release magnetic, electromagnetic, kinetic or thermal energy, or non-magnetic, non-thermal, non-electromagnetic or non-kinetic energy.

Another object of the present invention is to provide methods for treating anal incontinence disease.

Accordingly, in accordance with a first alternative there is provided a method of treating anal incontinence disease, comprising the steps of implanting an operable restriction device in a patient engaging the colon or rectum to form a restricted fecal passageway in the colon or rectum, providing a source of energy for energizing the restriction device, and controlling the source of energy to release energy for use in connection with the operation of the restriction device. The method may further comprise using energy released from the source of energy to operate the restriction device to enlarge and reduce, respectively, the fecal pasageway.

In accordance with a second alternative there is provided a method-of treating anal incontinence disease, comprising the steps of placing at least two laparascopical trocars in a patient'sbody, inserting a dissecting tool through the trocars and dissecting an area of the colon or rectum, placing an operable restriction device in the dissected area, so that the restriction device engages the colon close to the cardia or engages the rectum to form a restricted fecal passageway in the colon or rectum, implanting a source of energy in the patient, and controlling the implanted source of energy from outside the patient's body to release energy for use in connection with the operation of the restriction device.

In accordance with a third alternative there is provided a method of treating anal incontinence disease, comprising the steps of placing at least two laparascopical trocars in a patient's body, inserting a dissecting tool through the trocars and dissecting an area of the colon or rectum, implanting an operable restriction device in the dissected area, so that the restriction device engages the colon rectum to form a restricted fecal passageway in the colon or rectum, implanting an energy transfer device in the patient, providing an external source of energy, controlling the external source of energy to release wireless energy, and transferring the wireless energy by the energy transfer device into energy for use in connection with the operation of the restriction device.

BRIEF DESCRIPTION OF THE DRAWINGS

FIGS. 1 to 4 are schematic block diagrams illustrating four embodiments, respectively, of the invention, in which wireless energy is released from an external source of energy;

FIG. 9 is a schematic block diagram illustrating conceivable combinations of implanted components for achieving various communication options;

Referring to the drawing figures, like reference numerals designate identical or corresponding elements throughout the several figures.

DETAILED DESCRIPTION OF THE DRAWINGS

Figure 4:
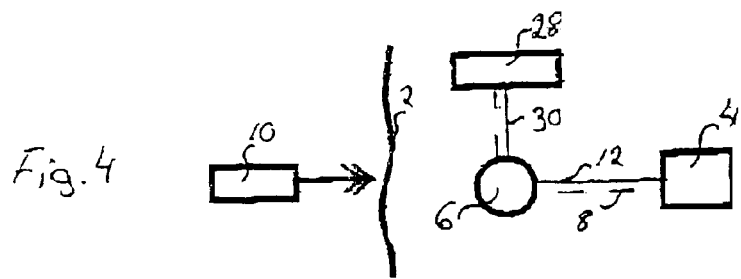

FIG. 1 schematically shows an embodiment of the anal incontinence disease apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable restriction device 4, which engages the patient's colon (or alternatively engages the rectum) to form a restricted fecal passageway in the colon. The restriction device 4 is capable of performing a reversible function, i.e. to enlarge and reduce the cross-sectional area of the fecal passageway, whereby the restriction device works as an artificial sphincter. An implanted control unit 6 controls the restriction device 4 via a control line 8 to form an adequate size of the cross-section area of the restricted fecal passageway. An external control unit 10 includes an external source of energy and a wireless remote control transmitting a control signal generated by the external source of energy. The control signal is received by a signal receiver incorporated in the implanted control unit 6, whereby the control unit 6 controls the implanted restriction device 4 in response to the control signal. The implanted control unit 6 also uses energy from the control signal for operating the restriction device 4 via a power supply line 12.

FIG. 2 shows an embodiment of the invention identical to that of FIG. 1, except that a reversing device in the form of a switch 14 operable by energy also is implanted in the patient for reversing the restriction device 4. The control unit 6 uses the switch 14 to reverse the function performed by the restriction device 4. More precisely, the external control unit 10 releases energy carried by a wireless signal and the implanted control unit 6 transfers the wireless energy into a current for operating the switch 14. When the control unit 6 shifts the polarity of the current the switch 14 reverses the function performed by the restriction device 4.

FIG. 3 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to reduce the cross-sectional area of the fecal passageway, and hydraulic fluid is pumped by the motor/pump unit 18 back from the restriction device 4 to the reservoir 20 to enlarge the cross-sectional area. The external control unit 10 releases energy carried by a wireless-signal and the implanted control unit 6 transfers the wireless energy into a current, for example a, current, for powering the motor/pump unit 18 via an electric power supply line 24. The implanted control unit 6 controls the motor/pump unit 16 and the restriction device 4 via control lines 26 and 27.

FIG. 4 shows an embodiment of the invention identical to that of FIG. 1, except that an accumulator 28 also is implanted in the patient. The control unit 6 stores energy received from the external control unit 10 in the accumulator 28. In response to a control signal from the external control unit 10 the implanted control unit 6 releases energy from the accumulator 28 via a power line 30 for the operation of the restriction device 4.

Figure 5:
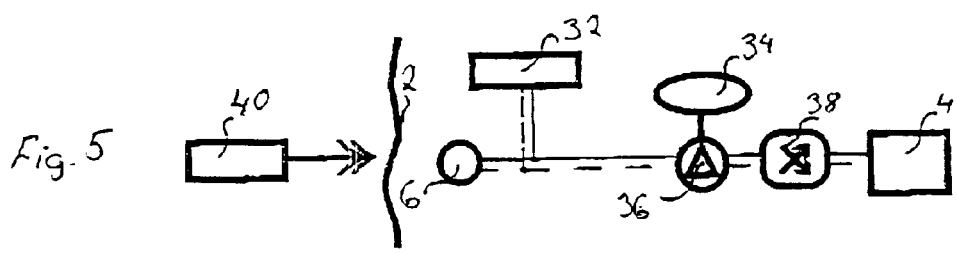
FIGS. 5 to 8 are schematic block diagrams illustrating four embodiments, respectively, of the invention, in which energy is released from an implanted source of energy.

FIG. 5 shows an embodiment of the invention comprising the restriction device 4, hydraulically operated, and the implanted control unit 6, and further comprising a source of energy in the form of a battery 32, a hydraulic fluid reservoir 34, a motor/pump unit 36 and a reversing device in the form of a hydraulic valve shifting device 38, all of which are implanted in the patient. The motor of the motor/pump unit 36 is an electric motor. An external control unit 40 includes a wireless remote control transmitting a control signal which is received by the signal receiver incorporated in the implanted control unit 6.

In response to a control signal from the external control unit 40 the implanted control unit 6 powers the motor/pump unit 36 with energy from the battery 32, whereby the motor/pump unit 36 distributes hydraulic fluid between the reservoir 34 and the restriction device 4. The control unit 6 controls the shifting device 38 to shift the hydraulic fluid flow direction between one direction in which the fluid is pumped by the motor/pump unit 36 from the reservoir 34 to the restriction device 4 to reduce the cross-sectional area of the fecal passageway, and another opposite direction in which the fluid is pumped by the motor/pump unit 36 back from the restriction device 4 to the reservoir 34 to enlarge the cross-sectional area.

Figure 6:
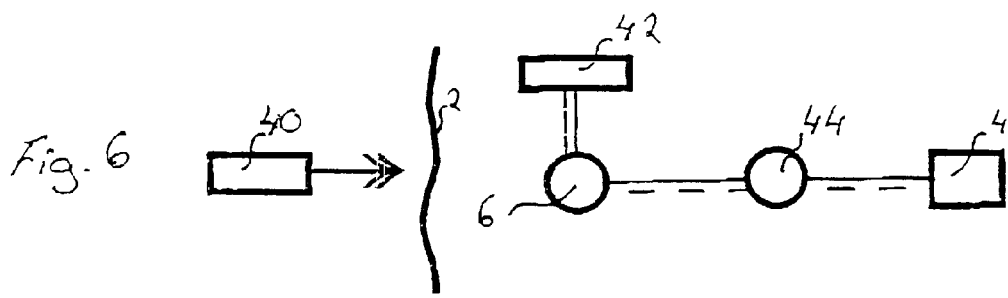

FIG. 6 shows an embodiment of the invention identical to that of FIG. 4, except that a battery 42 is substituted for the accumulator 28, the external control unit 40 of the embodiment of FIG. 5 is substituted for the external control unit 10 and an electric motor 44 is implanted in the patient for operating the restriction device 4. In response to a control signal from the external control unit 40 the implanted control unit 6 powers the motor 44 with energy from the battery 42, whereby the motor 44 operates the restriction device 4.

Figure 7:
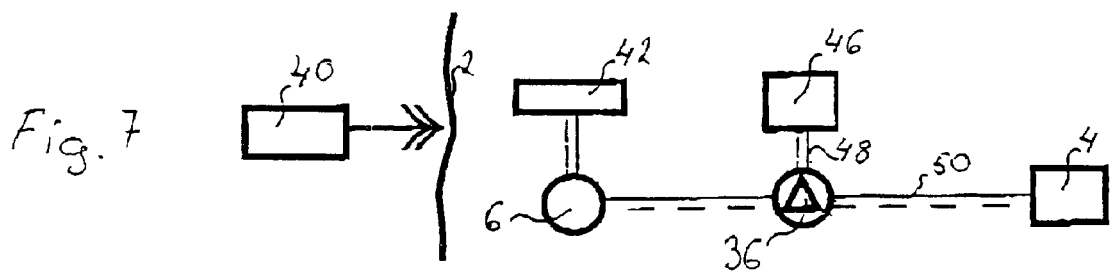

FIG. 7 shows an embodiment of the invention identical to that of FIG. 6, except that the motor/pump unit 36 of the embodiment of FIG. 5 is substituted for the motor 44 and a fluid reservoir 46 also implanted in the patient and via fluid conduits 48 and 50 connected to the motor/pump unit 36 and the restriction device 4, which in this case is hydraulically operated. In response to a control signal from the external control unit 40 the implanted control unit 6 powers the electric motor of the motor/pump unit 36 with energy from the battery 42, whereby the motor/pump unit 36 distributes hydraulic fluid between the fluid reservoir 46 and the restriction device 4.

Figure 8:
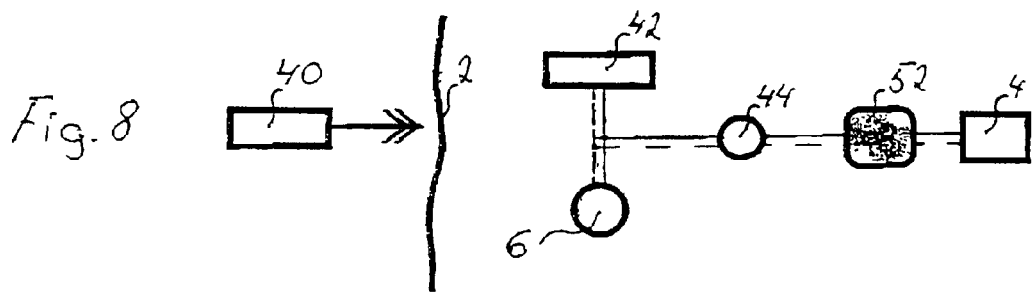

FIG. 8 shows an embodiment of the invention identical to that of FIG. 6, except that a mechanical reversing device in the form of a gear box 52 also is implanted in the patient. The implanted control unit 6 controls the gear box 52 to reverse the function performed by the restriction device 4 (mechanically operated).

FIG. 9 schematically shows conceivable combinations of implanted components of the apparatus for achieving various communication possibilities. Basically, there are the implanted restriction device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted restriction device 4 in response to the control signal.

A sensor 54 may be implanted in the patient for sensing a physical parameter of the patient, such as the pressure in the fecal passageway. The control unit 6, or alternatively the external control unit 10, may control the restriction device 4 in response to signalsfrom the sensor 54. A tranceiver may be combined with the sensor 54 for sending information on the sensed physical parameter to the external control unit 10. The wireless remote control of the external control unit 10 may comprise a signal transmitter or tranceiver and the implanted control unit 6 may comprise a signal receiver or transceiver. Alternatively, the wireless remote control of the external control unit 10 may comprise a signal reciever or transceiver and the implanted control unit 6 may comprise a signal transmitter or transceiver. The above tranceivers, transmitters and receivers may be used for sending information or data related to the restriction device from inside the patient's body to the outside thereof.

The motor 44 may be implanted for operating the restriction device 4 and also the battery 32 may be implanted for powering the motor 44. The battery 32 may be equipped with a tranceiver for sending information on the charge condition of the battery.

Those skilled in the art will realize that the above various embodiments according to FIGS. 1-9 could be combined in many different ways. For example, the energy operated switch 14 could be incorporated in any of the embodiments of FIGS. 3,4,6-8, the hydraulic shifting device 38 could be incorporated in any of the embodiments of FIGS. 3 and 7, and the gear box 52 could be incorporated in any of the embodiments of FIGS. 1,4 and 6.

Figure 10:
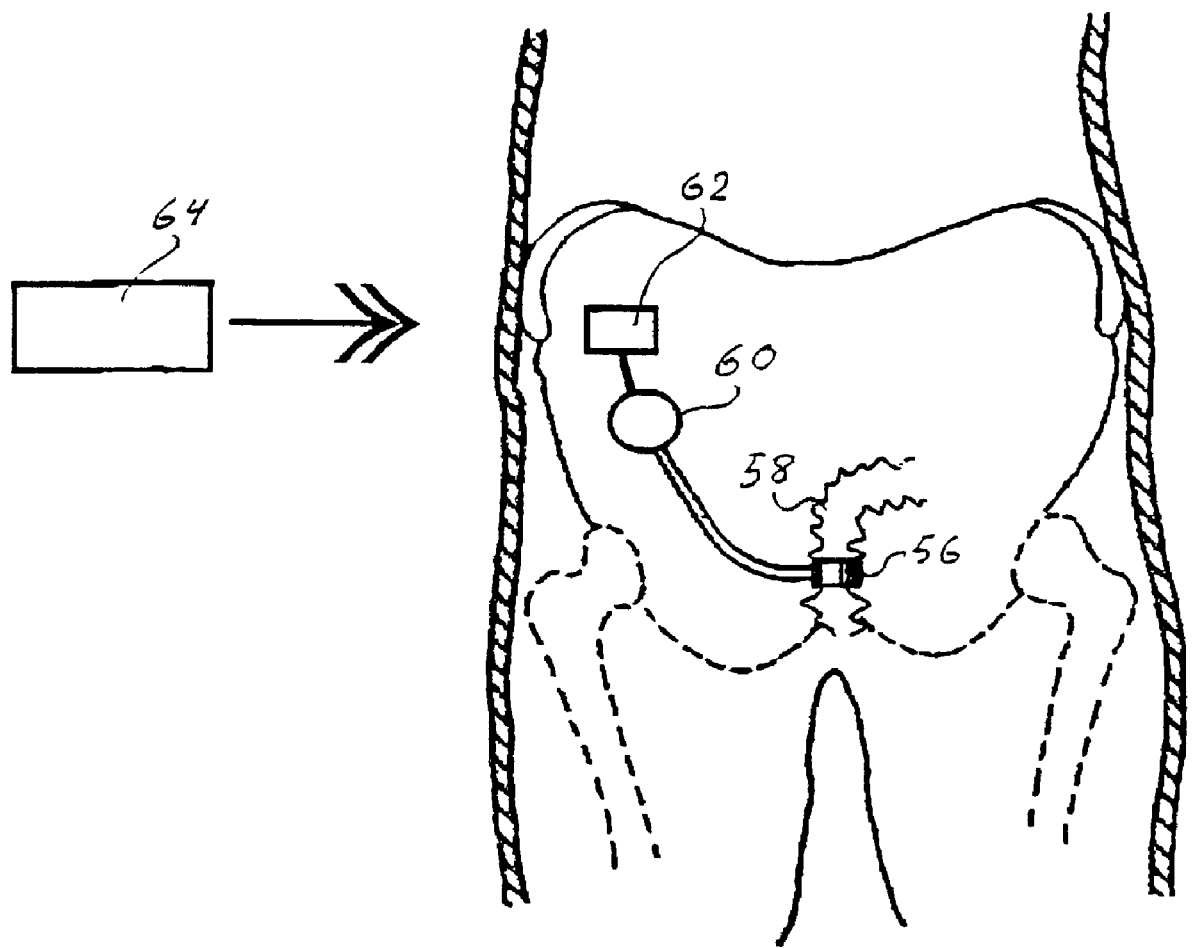
FIG. 10 illustrates the apparatus in accordance with the invention implanted in a patient.

FIG. 10 illustrates how any of the above-described embodiments of the anal incontinence disease treatment apparatus of the invention may be implanted in a patient. Thus, an assembly of the apparatus implanted in the patient comprises a restriction device 56 engaging the rectum 58, and an operation device 60 for operating the restriction device 56 and an internal control unit 62, which includes a signal receiver, for controlling the operation device 60. An external control unit 64 includes a signal transmitter for transmitting a control signal to the signal receiver of the implanted control unit 62. The implanted control unit 62 is capable of transferring signal energy from the control signal into electric energy for powering the operation device 60 and for energizing energy consuming implanted components of the apparatus.

Figure 11:
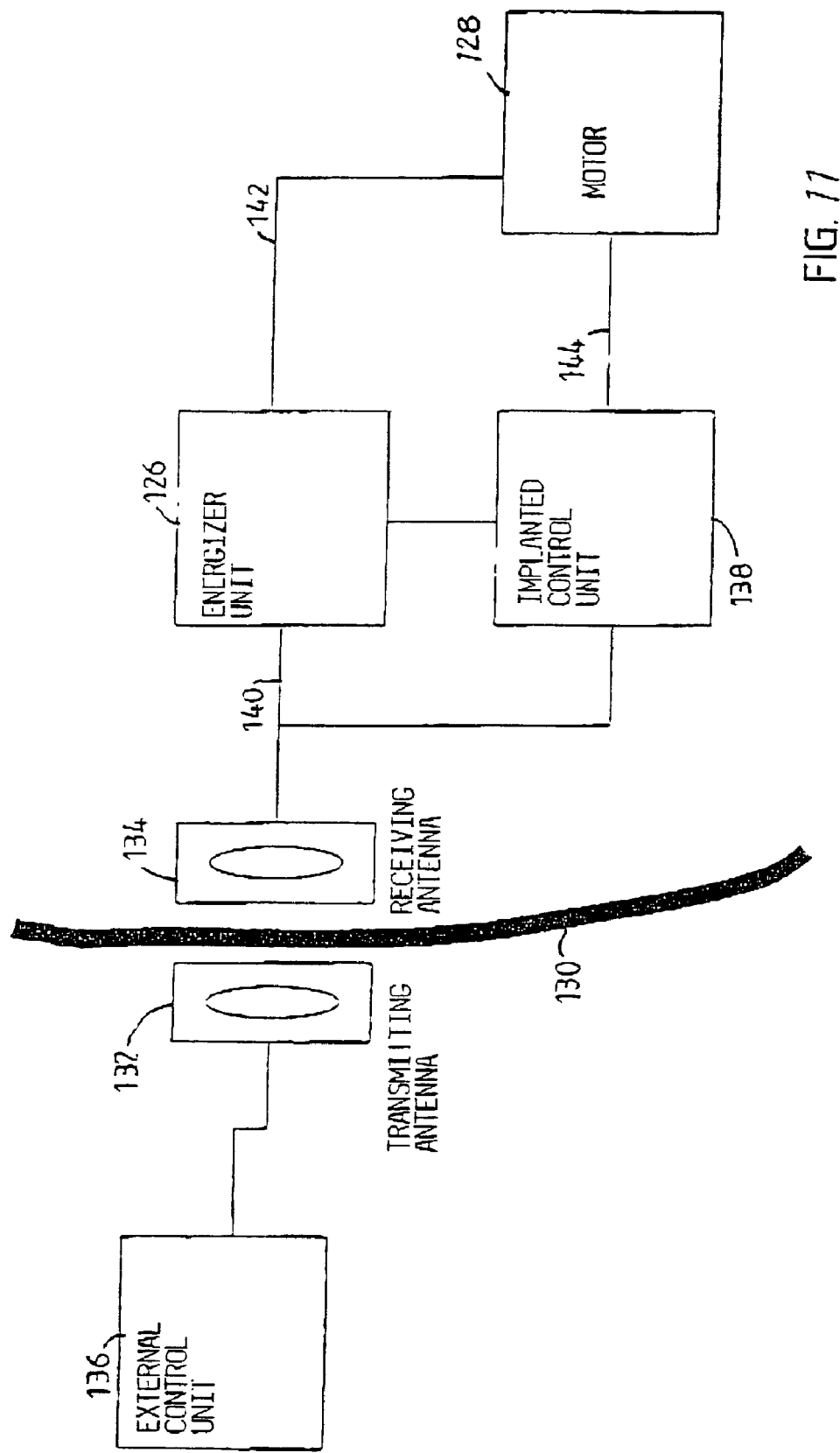
FIG. 11 is a block diagram illustrating remote control components of an embodiment of the invention.

FIG. 11 shows the basic parts of a wireless remote control of the apparatus of the invention including an electric motor 128 for operating a restriction member, for example of the type illustrated in FIG. 10. In this case, the remote control is based on the transmission of electromagnetic wave signals, often of high frequencies in the order of 100 kHz-1 gHz, through the skin 130 of the patient. In FIG. 11, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the restriction device. The microprocessor starts a command by applying a high frequency signal on the antenna 132. After a short time, when the signal has energized the implanted parts of the control system, commands are sent to contract or enlarge the restriction device in predefined steps. The commands are sent as digital packets in the form illustrated below.

| Start pattern, 8 bits | Command, 8 bits | Count, 8 bits | Checksum, 8 bits |
|---|---|---|---|

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the restriction device depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect said battery to the control unit 138 in an on mode when said switch is powered by said power supply and to keep said battery disconnected from the control unit in a standby mode when said switch is unpowered.

Figure 12:
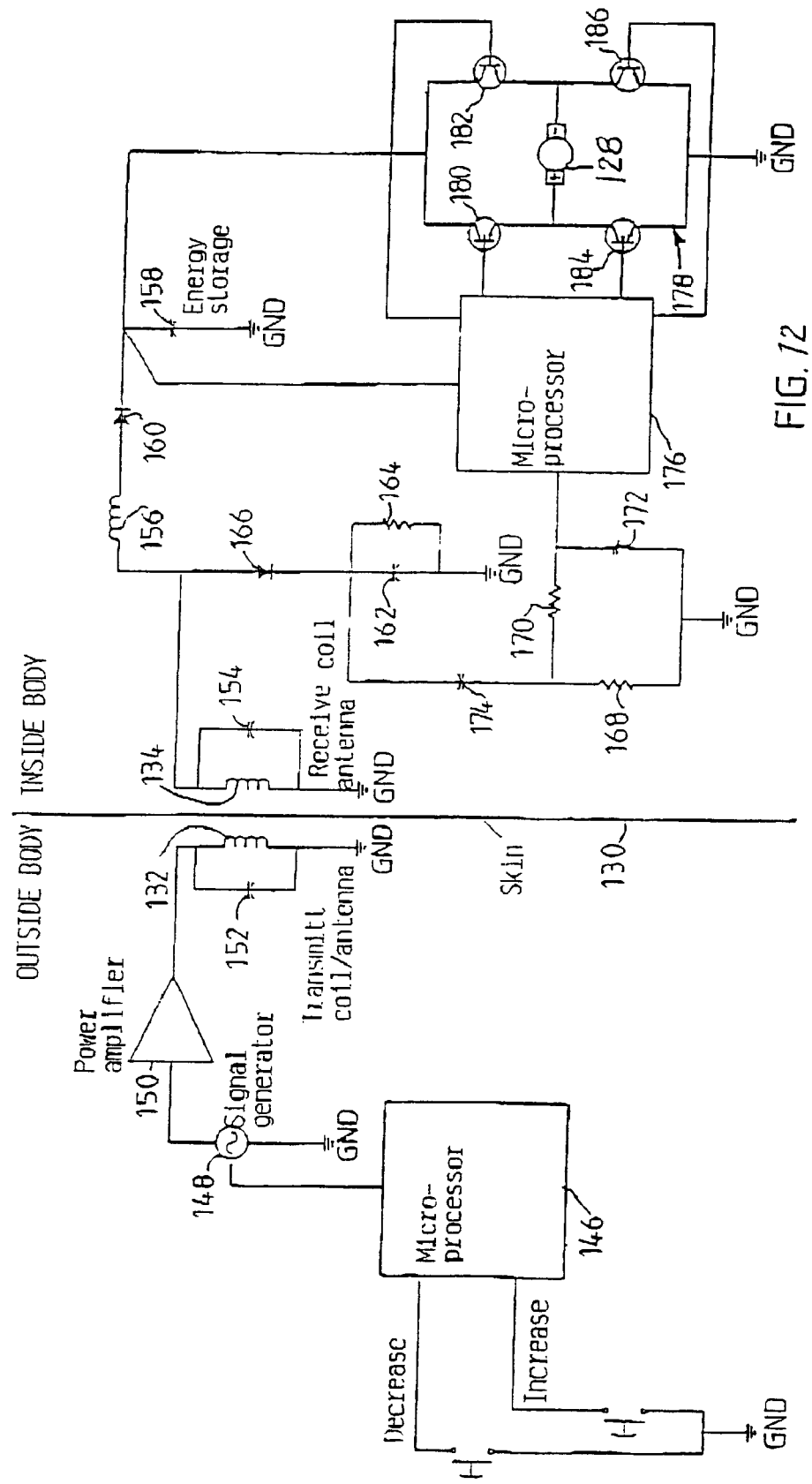
FIG. 12 is a schematic view of exemplary circuitry used for the components of the block diagram of FIG. 11.

With reference to FIG. 12, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168,170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

In the practice of the present invention the details of the elongated restriction device 4, 56 (such as a band) and the adjustment/operation device (which may have electric, hydraulic, or mechanical, etc. actuation) 6, 60 may be as described in copending application Ser. No. 09/133,319, filed Aug. 13, 1998, Ser. No. 09/133,320, filed Aug. 13, 1998 and Ser. No. 09/133,322, filed Aug. 13, 1998, the disclosures of which are incorporated by reference herein.

The invention also comprises or consists of the foregoing structures and method steps, and is to be interpreted as broadly as allowed by the prior art.

What is claimed is:

1. An anal incontinence disease treatment apparatus, comprising:
   a restriction device implantable in a patient that is operable to perform a reversible function involving enlarging and restricting the fecal passageway;
   an internal source of energy implantable in a patient for energizing said restriction device; and
   a control device operable from outside the patient's body for releasing energy from said source of energy, said released energy being used in connection with the operation of said restriction device,
   an implantable stabilizer comprising a capacitor or a rechargeable accumulator for stabilizing the energy released by said control device, and
   wherein the control device comprises:
      a first control unit operable from outside of the patients body for providing a signal, and
      a second control unit implantable in a patient adapted to control the restriction device to open and close the fecal passageway in response to the signal.

2. The apparatus according to claim 1, wherein said control device controls said restriction device to close the fecal passageway to prevent feces from passing therethrough and to enlarge the fecal passageway to allow feces to readily pass therethrough.

3. The apparatus according to claim 2, wherein said second control unit is programmable.

4. The apparatus according to claim 3, wherein said second control unit being programmable by said first control unit.

5. The apparatus according to claim 4, wherein said first control unit loads said second control unit with data in accordance with a loading mode only authorized for a doctor.

6. The apparatus according to claim 4, wherein said first control unit controls said second control unit in accordance with a doctor mode only authorized for a doctor.

7. The apparatus according to claim 4, wherein said first control unit controls said second control unit in accordance with a patient mode permitted for the patient.

8. The apparatus according to claim 3, wherein said second control unit is programmable for controlling said restriction device over time.

9. The apparatus according to claim 8, wherein said second control unit controls said restriction device over time in accordance with an activity schedule program.

10. The apparatus according to claim 8, wherein said second control unit comprises a microprocessor.

11. The apparatus according to claim 1, further comprising an operation device implanted in the patient for operating said restriction device, wherein said control device controls said operation device to operate said restriction device.

12. The apparatus according to claim 11, wherein said control device shifts polarity of said released energy to reverse said operation device.

13. The apparatus according to claim 11, wherein said operation device comprises an electric motor and said released energy comprises electric energy.

14. The apparatus according to claim 11, wherein said restriction device is operable to perform a reversible function.

15. The apparatus according to claim 1, wherein said internal source of energy comprises at least one accumulator, at least one capacitor or at least one rechargeable battery, or a combination of at least one capacitor and at least one rechargeable battery.

16. The apparatus according to claim 15, wherein said internal source of energy comprises an electric source of energy.

17. The apparatus according to claim 16, wherein said electric source of energy comprises an accumulator, or a battery having a life-time of at least 10 years.

18. The apparatus according to claim 15, wherein said at least one accumulator, at least one capacitor or at least one rechargeable battery, or a combination of at least one capacitor and at least one rechargeable battery are implantable in the patient and are adapted to store energy released from an external wireless source of energy.

19. The apparatus according to claim 18, wherein said control device controls said stored energy to control said restriction device to close the fecal passageway to prevent feces from passing there through and to enlarge the fecal passageway to allow feces to readily pass there through.

20. The apparatus according to claim 1, further comprising at least one implanted sensor for sensing at least one physical parameter of the patient.

21. The apparatus according to claim 20, wherein said control device controls said restriction device in response to signals from said sensor.

22. The apparatus according to claim 21, wherein said second control unit directly controls said restriction device in response to signals from said sensor.

23. The apparatus according to claim 21, wherein said external first control unit controls said restriction device in response to signals from said sensor.

24. The apparatus according to claim 23, wherein said first control unit directly controls said restriction device in response to signals by said sensor.

25. The apparatus according to claim 23, wherein said first control unit stores information on said physical parameter sensed by said sensor and is manually operated to control said restriction device based on said stored information.

26. The apparatus according to claim 20, further comprising at least one implanted sender for sending information on said physical parameter sensed by said sensor.

27. The apparatus according to claim 1, further comprising an external data communicator outside the patient's body and an internal data communicator implantable in the patient for communicating with said external communicator, wherein said implantable communicator feeds data related to the patient back to said external communicator or said external communicator feeds data to said internal communicator.

28. The apparatus according to claim 27, wherein said implantable communicator feeds data related to said implanted restriction device.

29. The apparatus according to claim 27, wherein said implantable communicator feeds data related to at least one physical signal of the patient.

30. The apparatus according to claim 1, wherein said restriction device controls the cross-sectional area of said fecal passageway.

31. The apparatus according to claim 30, wherein said restriction device steplessly controls the cross-sectional area of said fecal passageway.

32. The apparatus according to claim 1, further comprising a pressure sensor for directly or indirectly sensing the pressure in said fecal passageway.

33. The apparatus according to claim 32, wherein said control device controls said restriction device in response to signals from said pressure sensor.

34. The apparatus according to claim 1, wherein said control device releases energy for a determined time period.

35. The apparatus according to claim 1, wherein said control device releases energy in a determined number of energy pulses.

36. The apparatus according to claim 1, wherein said control device comprises a wireless remote control transmitting at least one wireless control signal for controlling said restriction device.

37. The apparatus according to claim 36, wherein said remote control is capable of obtaining information on the condition of said restriction device and to control said restriction device in response to said information.

38. The apparatus according to claim 36, wherein said wireless remote control comprises at least one external signal transmitter or transceiver and at least one internal signal receiver or transceiver implantable in the patient.

39. The apparatus according to claim 36, wherein said wireless remote control comprises at least one external signal receiver or transceiver and at least one internal signal transmitter or transceiver implantable in the patient.

40. The apparatus according to claim 36, wherein said remote control is capable of sending information related to said restriction device from inside the patient's body to the outside thereof.

41. The apparatus according to claim 40, wherein said remote control controls said restriction device in response to said information.

42. The apparatus according to claim 36, wherein said remote control transmits a carrier signal for carrying said control signal.

43. The apparatus according to claim 42, wherein said carrier signal is frequency, amplitude or frequency and amplitude modulated.

44. The apparatus according to claim 42, wherein said carrier signal is digital, analog or digital and analog.

45. The apparatus according to claim 42, wherein said control signal used with said carrier signal is frequency, amplitude or frequency and amplitude modulated.

46. The apparatus according to claim 36, wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

47. The apparatus according to claim 36, wherein said control signal comprises an electric, magnetic or electric and magnetic field.

48. The apparatus according to claim 36, wherein said control signal is digital, analog or digital and analog.

49. The apparatus according to claim 48, wherein said remote control transmits an electromagnetic carrier wave signal for carrying said digital or analog control signal.

50. The apparatus according to claim 36, wherein said control signal is transmitted in pulses by said wireless remote control.

51. The apparatus according to claim 1, wherein said released energy is electrical energy.

52. The apparatus according to claim 1, wherein said control device releases energy from said source of energy in a non-invasive manner.

53. The apparatus according to claim 1, wherein said control device releases electromagnetic energy.

54. The apparatus according to claim 1, wherein said control device releases energy from said source of energy in a mechanical manner.

55. The apparatus according to claim 1, wherein said control device releases non-magnetic energy.

56. The apparatus according to claim 1, wherein said control device releases non-electromagnetic energy.

57. The apparatus according to claim 1, wherein said control device releases non-kinetic energy.

58. The apparatus according to claim 1, wherein said control device releases non-thermal energy.

59. The apparatus according to claim 1, wherein released energy is used to open and close the fecal passageway.

60. The apparatus according to claim 1, wherein said restriction device is non-inflatable.

61. The apparatus according to claim 1 or 60 further comprising a wireless energy transmitter and an implantable coil adapted to receive wireless energy transmitted by said wireless energy transmitter and further comprising a capacitor connected in parallel with said coil, wherein said coil forms together with said capacitor a resonant circuit tuned to a frequency generated by the wireless energy transmitter.

62. The apparatus according to claim 1 or 60, wherein said control device release energy from the source of energy for a determined time period or in a determined number of energy pulses.

* * * * *